United States Patent
Verhoogen

(10) Patent No.: US 8,845,644 B1
(45) Date of Patent: Sep. 30, 2014

(54) ORTHOPEDIC SURGICAL INSTRUMENT SET AND A METHOD INCLUDING THE SAME

(71) Applicant: Alex Rene Verhoogen, Mansfield, OH (US)

(72) Inventor: Alex Rene Verhoogen, Mansfield, OH (US)

( * ) Notice: Subject to any disclaimer, the term of this patent is extended or adjusted under 35 U.S.C. 154(b) by 0 days.

(21) Appl. No.: 14/059,357

(22) Filed: Oct. 21, 2013

Related U.S. Application Data

(60) Provisional application No. 61/716,925, filed on Oct. 22, 2012.

(51) Int. Cl.
| | | |
|---|---|---|
| *A61F 5/00* | (2006.01) | |
| *A61F 2/46* | (2006.01) | |
| *A61B 17/17* | (2006.01) | |
| *A61B 17/16* | (2006.01) | |
| *A61B 17/14* | (2006.01) | |

(52) U.S. Cl.
CPC ......... *A61B 17/1764* (2013.01); *A61B 17/1655* (2013.01); *A61B 17/141* (2013.01)
USPC .......................................... 606/87; 606/86 R

(58) Field of Classification Search
USPC ................. 606/79–86 R, 167, 178, 184, 185; 407/29.1, 29.13, 29.15; 408/204, 206
See application file for complete search history.

(56) References Cited

U.S. PATENT DOCUMENTS

| | | | | |
|---|---|---|---|---|
| 6,110,209 | A * | 8/2000 | Stone | 623/16.11 |
| 6,592,588 | B1 * | 7/2003 | Bobic et al. | 606/79 |
| 2004/0030343 | A1 * | 2/2004 | Kurc | 606/80 |
| 2007/0135924 | A1 | 6/2007 | Verhoogen | |
| 2008/0255623 | A1 * | 10/2008 | Steiner et al. | 606/86 R |
| 2009/0299372 | A1 * | 12/2009 | Steiner et al. | 606/79 |
| 2012/0053641 | A1 * | 3/2012 | Meridew | 606/86 R |

* cited by examiner

*Primary Examiner* — Matthew Lawson
(74) *Attorney, Agent, or Firm* — The Law Office of Patrick F. O'Reilly III, LLC

(57) ABSTRACT

An orthopedic surgical instrument set is disclosed herein. The instrument set includes (i) at least one tamp, the tamp including a substantially cylindrical body portion; (ii) at least one trephine, the trephine having a first end and a second end, the second end of the trephine having a plurality of teeth disposed thereon, the trephine being provided with a cylindrical passageway disposed therethrough for receiving the substantially cylindrical body portion of the tamp; and (iii) a guide stand having a base portion and an upper portion disposed above the base portion, the upper portion of the guide stand being provided with a guide aperture disposed therein for receiving the at least one trephine. A method of fabricating a bone plug, which utilizes the orthopedic surgical instrument set, is also disclosed herein.

20 Claims, 13 Drawing Sheets

SECTION A-A

SECTION B-B

SECTION C-C

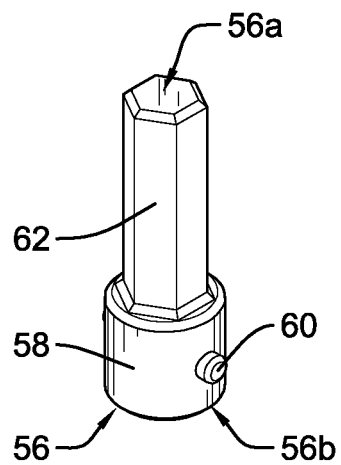
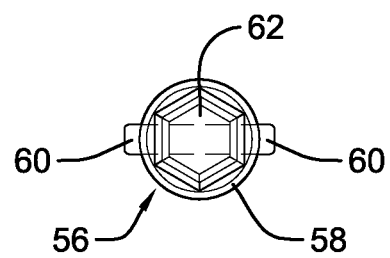
FIG. 19  FIG. 20
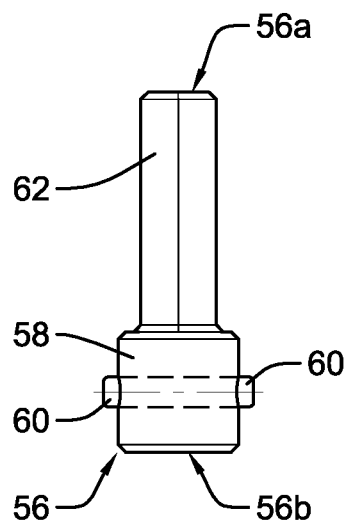
FIG. 21

ORTHOPEDIC SURGICAL INSTRUMENT SET AND A METHOD INCLUDING THE SAME

CROSS-REFERENCE TO RELATED APPLICATIONS

This patent application claims priority to, and incorporates by reference in its entirety, U.S. Provisional Patent Application No. 61/716,925, entitled "Orthopedic Surgical Instrument Set And A Method Including The Same", filed on Oct. 22, 2012.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to an orthopedic surgical instrument set. More particularly, the invention relates to an orthopedic surgical instrument set that is capable of being used to harvest and insert a bone plug during orthopedic surgery.

2. Background and Description of Related Art

A total knee replacement is a surgical procedure in which the weight-bearing surfaces of a damaged knee joint are replaced by an artificial knee implant. The artificial knee implant comprises femoral and tibial components that glide together to replicate the knee joint. These components are typically composed of metal and a durable plastic, such as polyethylene. Before these components of the prosthetic knee can be implanted, both the distal end of the femur (thigh bone) and the proximal end of the tibia (shin bone) must be resurfaced.

Prior to resurfacing the distal femur for most total knee systems, an approximately 8 to 10 mm hole is drilled in the distal femur for receiving an intramedullary rod of a femoral cutting guide or jig. The femoral cutting guide or jig allows the orthopedic surgeon to accurately remove portions of the distal femur so that the prosthetic knee can be precisely fitted on the patient. In particular, the femoral cutting guide enables the orthopedic surgeon to accurately cut a specific angle relative to the femur (e.g., approximately 5 to 7 degrees) and to remove one or more thin portions of the distal femur (e.g., with a thickness of approximately 8 mm to 10 mm).

Deleteriously, this 8-10 mm hole in the distal femur, which is used for receiving the intramedullary rod of the cutting guide or jig, allows for continued bleeding to occur during and after the procedure. It also occasionally allows for unwanted cement to enter into the femoral canal. A bone plug can be crudely fashioned to fill the hole, but this takes time, and often is poorly effective in completely filling the hole.

Therefore, what is needed is simple instrumentation that can be used to quickly harvest and introduce a bone plug for substantially filling and sealing the distal femoral intramedullary hole in total knee replacement arthroplasty, wherein the instrument set utilizes the bone normally discarded. Moreover, a surgical instrument set is needed that enables a slightly oversized bone plug to be quickly produced on the back table in an operating room, and easily inserted into the distal femoral hole by the surgeon. Furthermore, there is a need for a surgical instrument set that is configured to be used with a conventional orthopedic drill.

BRIEF SUMMARY OF EMBODIMENTS OF THE INVENTION

Accordingly, the present invention is directed to an orthopedic surgical instrument set and a method including the same that substantially obviates one or more problems in the art hereinbefore discussed.

In accordance with one or more embodiments of the present invention, there is provided an orthopedic surgical instrument set, which includes: (i) at least one tamp, the tamp including a substantially cylindrical body portion; (ii) at least one trephine, the trephine having a first end and a second end, the second end of the trephine having a plurality of teeth disposed thereon, the trephine being provided with a cylindrical passageway disposed therethrough for receiving the substantially cylindrical body portion of the tamp; and (iii) a guide stand having a base portion and an upper portion disposed above the base portion, the upper portion of the guide stand being provided with a guide aperture disposed therein for receiving the at least one trephine.

In a further embodiment of the present invention, the at least one tamp further includes a cylindrical head located at one end of the substantially cylindrical body portion, the cylindrical head having an outer diameter that is greater than that of the substantially cylindrical body portion.

In yet a further embodiment, an axial length of the cylindrical passageway of the at least one trephine is substantially equal to an axial length of the substantially cylindrical body portion of the at least one tamp.

In still a further embodiment, the at least one trephine further includes a collar disposed proximate to the first end thereof.

In yet a further embodiment, when the at least one tamp is fully inserted into the at least one trephine, a bottom surface of the cylindrical head of the at least one tamp abuts a top annular surface of the at least one trephine.

In still a further embodiment, the at least one trephine further includes a plurality of slots cut in the first end thereof.

In yet a further embodiment, the orthopedic surgical instrument set further comprises a bit attachment member, the bit attachment member having a first end and a second end, the first end of the bit attachment member being configured to engage with a chuck of a surgical drill, the second end of the bit attachment member having opposed protruding portions disposed proximate thereto.

In still a further embodiment, each of the opposed protruding portions of the bit attachment member are configured to matingly engage with a respective one of the plurality of slots in the at least one trephine.

In yet a further embodiment, the at least one tamp comprises two tamps and the at least one trephine comprises two trephines, and wherein the substantially cylindrical body portion of a first of the two tamps has a first outside diameter; the substantially cylindrical body portion of a second of the two tamps has a second outside diameter that is larger than the first outside diameter of the first tamp; the cylindrical passageway of a first of the two trephines has a first inner diameter that is slightly larger than the first outside diameter of the first tamp; and the cylindrical passageway of a second of the two trephines has a second inner diameter that is slightly larger than the second outside diameter of the second tamp.

In still a further embodiment, the guide stand further includes a connecting portion disposed between the base portion and the upper portion.

In yet a further embodiment, the upper portion of the guide stand is spaced apart from the base portion of the guide stand by the connecting portion such that a gap is defined between the bottom surface of the upper portion and the top surface of the base portion.

In still a further embodiment, the at least one trephine further includes a collar disposed proximate to the first end thereof.

In yet a further embodiment, a vertical dimension of the guide stand measured between the top surface of the base portion and the top surface of the upper portion is slightly less than an axial length of the at least one trephine measured between a bottom surface of the collar and the second end of the at least one trephine.

In still a further embodiment, the base portion of the guide stand is provided with a kerf disposed therein for receiving the second end of the at least one trephine.

In yet a further embodiment, the kerf is in the form of one of: (i) an annular slot and (ii) a cylindrical cavity.

In accordance with one or more other embodiments of the present invention, there is provided an orthopedic surgical instrument set, which includes: at least one tamp, the tamp including a substantially cylindrical body portion; at least one trephine, the trephine having a first end and a second end, the second end of the trephine having a plurality of teeth disposed thereon, the trephine being provided with a cylindrical passageway disposed therethrough for receiving the substantially cylindrical body portion of the tamp; and a guide stand having a base portion, an upper portion disposed above the base portion, and a connecting portion disposed between the base portion and the upper portion, the upper portion of the guide stand being provided with a guide aperture disposed therein for receiving the at least one trephine, and the upper portion of the guide stand being spaced apart from the base portion of the guide stand by the connecting portion such that a gap is defined between the bottom surface of the upper portion and the top surface of the base portion.

In accordance with yet one or more other embodiments of the present invention, there is provided a method of fabricating a bone plug for use during an orthopedic surgical procedure, the method comprising the steps of: (i) providing an orthopedic surgical instrument set that includes: at least one tamp, the tamp including a substantially cylindrical body portion; at least one trephine, the trephine having a first end and a second end, the second end of the trephine having a plurality of teeth disposed thereon, the trephine being provided with a cylindrical passageway disposed therethrough for receiving the substantially cylindrical body portion of the tamp; and a guide stand having a base portion and an upper portion disposed above the base portion, the upper portion of the guide stand being provided with a guide aperture disposed therein for receiving the at least one trephine; (ii) positioning a fragment of bone on the base portion of the guide stand; (iii) positioning the at least one trephine in the guide aperture of the upper portion of the guide stand; (iv) cutting a bone plug from the fragment of bone by driving the plurality of teeth on the second end of the at least one trephine into the fragment of bone; (v) removing the at least one trephine containing the bone plug from the guide stand; (vi) inserting the at least one tamp into the at least one trephine; (vii) positioning the at least one trephine containing the bone plug over an aperture in a bone of patient; and (viii) driving the bone plug into the aperture of the bone of the patient by applying a force to an end of the at least one tamp.

In a further embodiment of the present invention, the base portion of the guide stand is provided with a kerf disposed therein for receiving the second end of the at least one trephine; and wherein the step of positioning the fragment of bone further comprises positioning the fragment of bone on the base portion of the guide stand overlying the kerf.

In yet a further embodiment, the method further comprises the steps of: providing a bit attachment member, the bit attachment member having a first end and a second end, the first end of the bit attachment member being configured to engage with a chuck of a surgical drill, the second end of the bit attachment member being configured to engage with the first end of the at least one trephine; providing a surgical drill having a chuck that is rotatably driven by a motor; engaging the first end of the bit attachment member with the chuck of the surgical drill; engaging the second end of the bit attachment member with the first end of the at least one trephine; and driving the plurality of teeth on the second end of the at least one trephine into the fragment of bone by rotating the at least one trephine using the surgical drill.

In still a further embodiment, a mallet is provided for applying the force to the at least one tamp; and wherein the step of driving the bone plug into the aperture further comprises driving the bone plug into the aperture of the bone of the patient by applying the force to the end of the at least one tamp by using the mallet.

It is to be understood that the foregoing background and general description, and the following detailed description of the preferred embodiment(s) of the present invention, are merely exemplary and explanatory in nature. As such, the foregoing background and general description, and the following detailed description of the preferred embodiment(s) of the invention, should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 19 is a perspective view of one bit attachment member of the orthopedic surgical instrument set according to an embodiment of the invention;

FIG. 20 is a top view of the bit attachment member of the orthopedic surgical instrument set according to an embodiment of the invention;

FIG. 21 is a side view of the bit attachment member of the orthopedic surgical instrument set according to an embodiment of the invention;

Throughout the figures, the same parts are always denoted using the same reference characters so that, as a general rule, they will only be described once.

DETAILED DESCRIPTION OF EMBODIMENTS OF THE INVENTION

Figure 1:
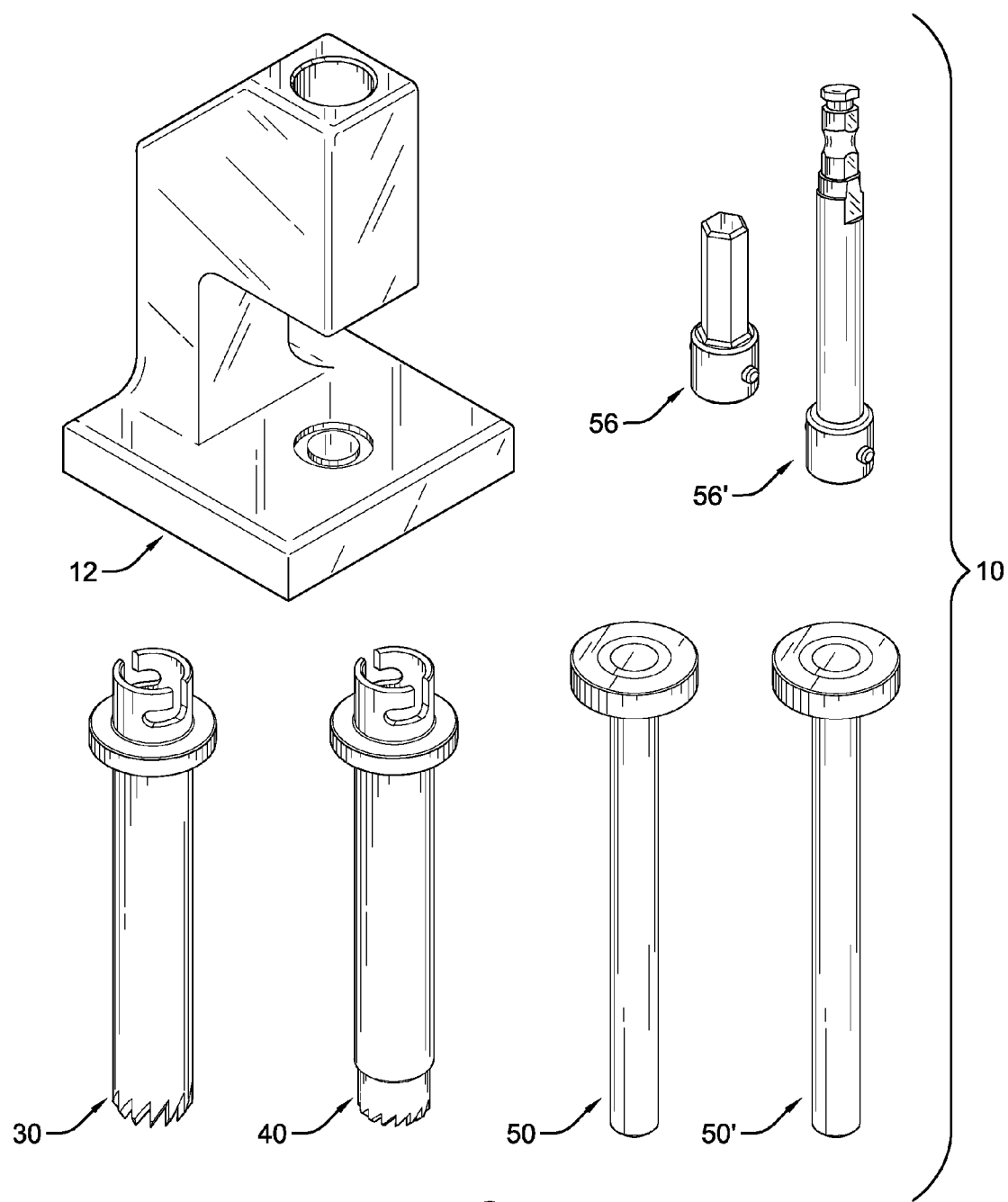
FIG. 1 is a perspective view of an orthopedic surgical instrument set according to an embodiment of the invention.
Figure 2:
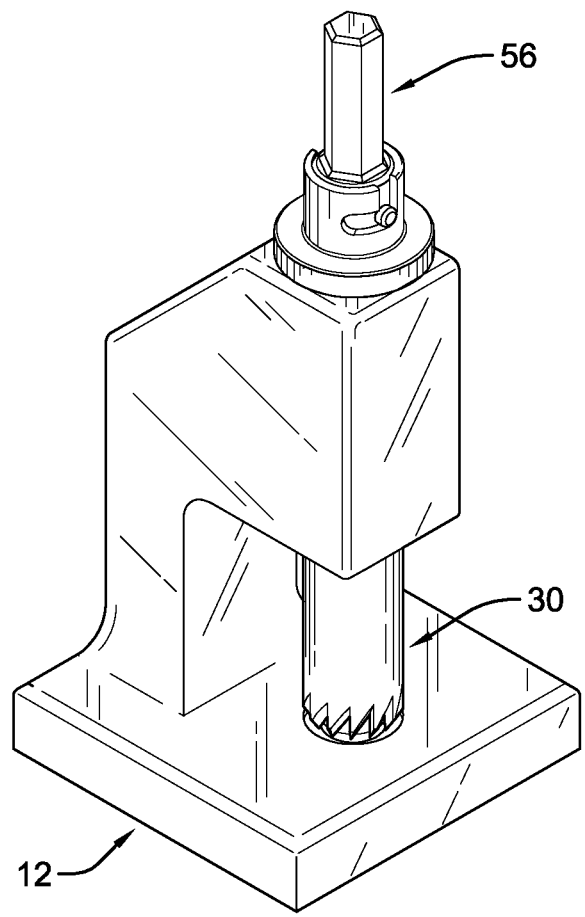
FIG. 2 is a perspective view illustrating components of the orthopedic surgical instrument set in an assembled state according to an embodiment of the invention.
Figure 3:
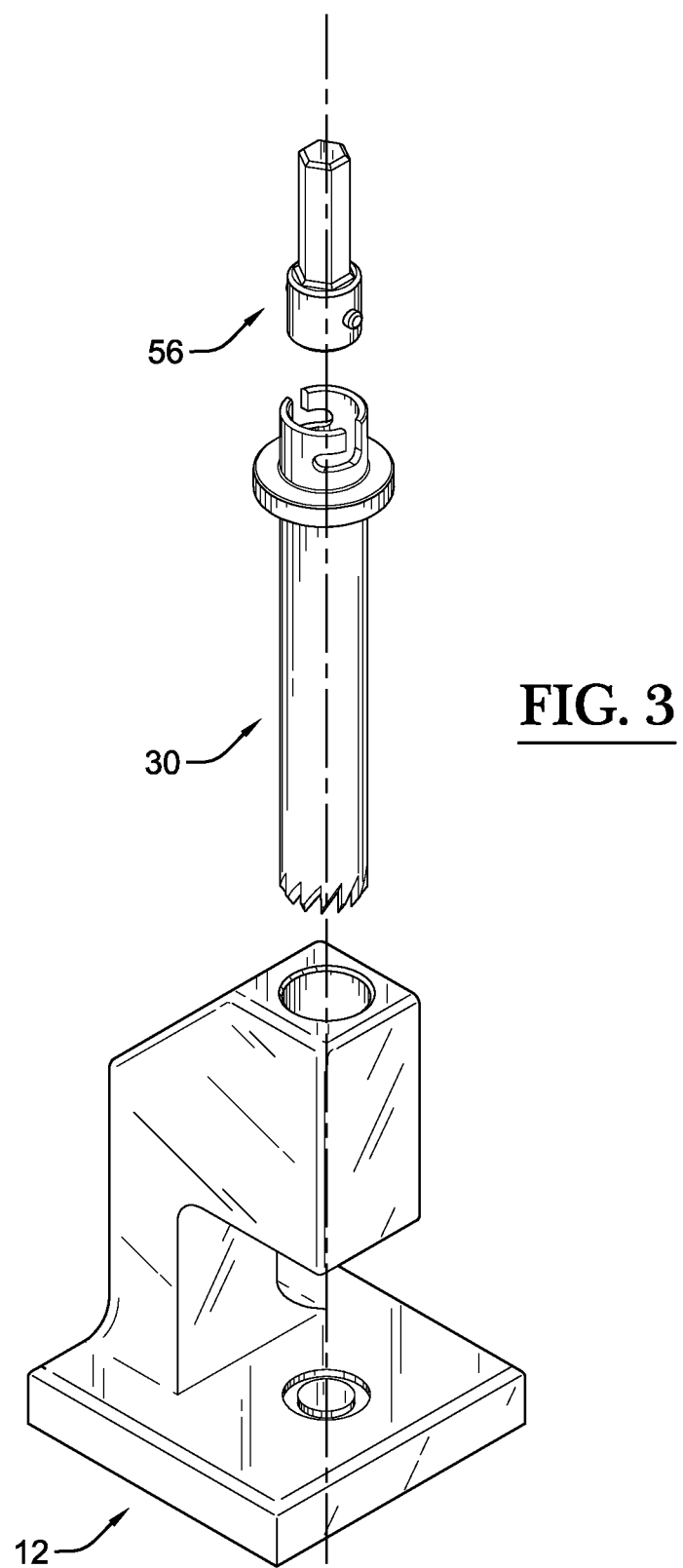
FIG. 3 is a perspective view illustrating components of the orthopedic surgical instrument set in an exploded state according to an embodiment of the invention.

An embodiment of the orthopedic surgical instrument set is seen generally at 10 in FIG. 1. The illustrated embodiment of the orthopedic surgical instrument set 10 generally comprises a guide stand 12, a first trephine 30, a second trephine 40, a first tamp 50, a second tamp 50', and a bit attachment member 56 or 56'. The first tamp 50 is designed to slidably engage with the first trephine 30, while the second tamp 50' is designed to slidingly engage with the second trephine 40. As shown in FIG. 2, the guide stand 12 is configured to hold the trephine 30 in place while the bone plug is being cut from a fragment of bone. In order to cut the bone plug, the trephine 30 or 40 is driven by a standard surgical drill via the bit attachment member 56 (or driver 56). Alternatively, depending on the configuration of the drill chuck, a bit attachment member 56' (or driver 56') can be used to connect the trephine 30 or 40 to the surgical drill. An exploded view of the guide stand 12, the first trephine 30, and the bit attachment member 56 is depicted in FIG. 3.

Figure 4:
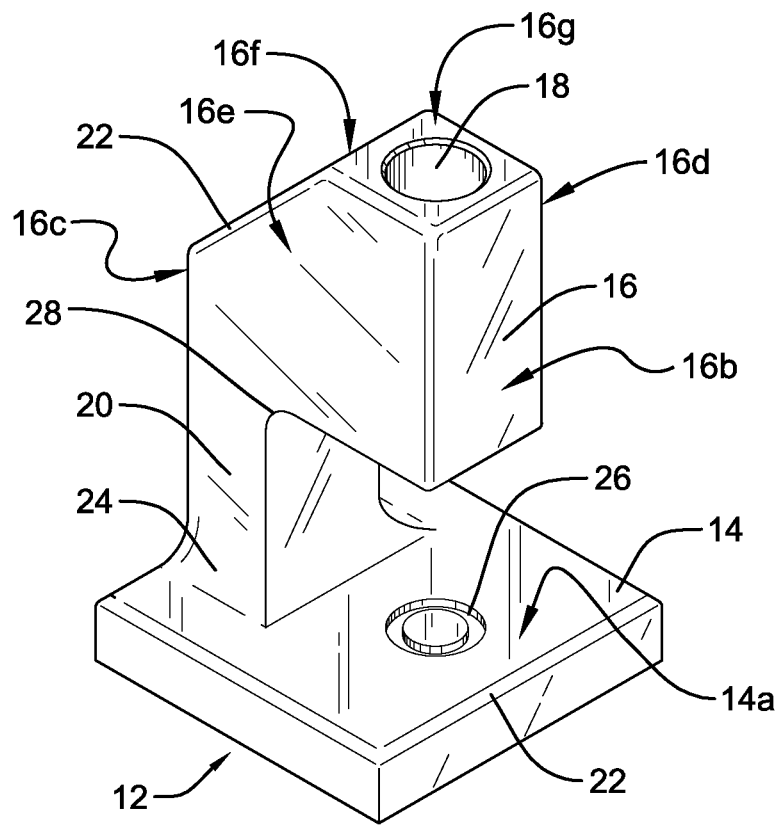
FIG. 4 is a perspective view of a guide stand of the orthopedic surgical instrument set according to an embodiment of the invention.
Figure 5:
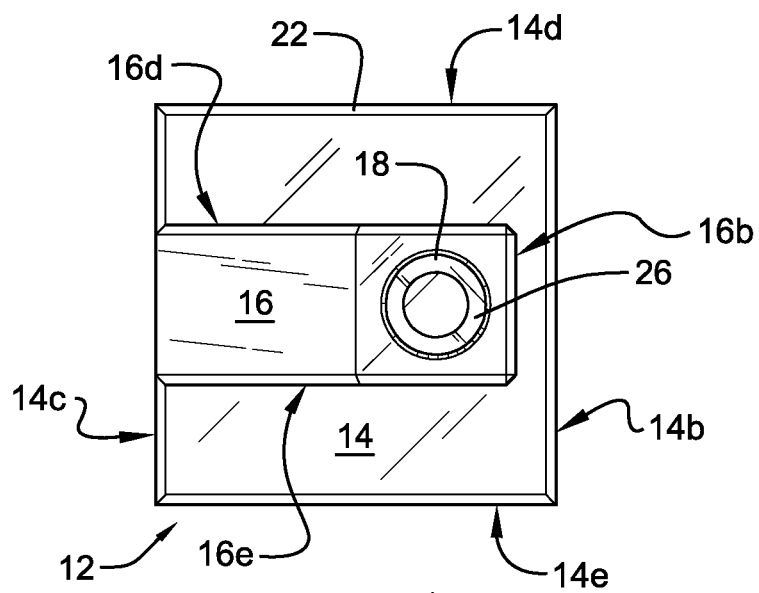
FIG. 5 is a top view of the guide stand of the orthopedic surgical instrument set according to an embodiment of the invention.
Figure 6:
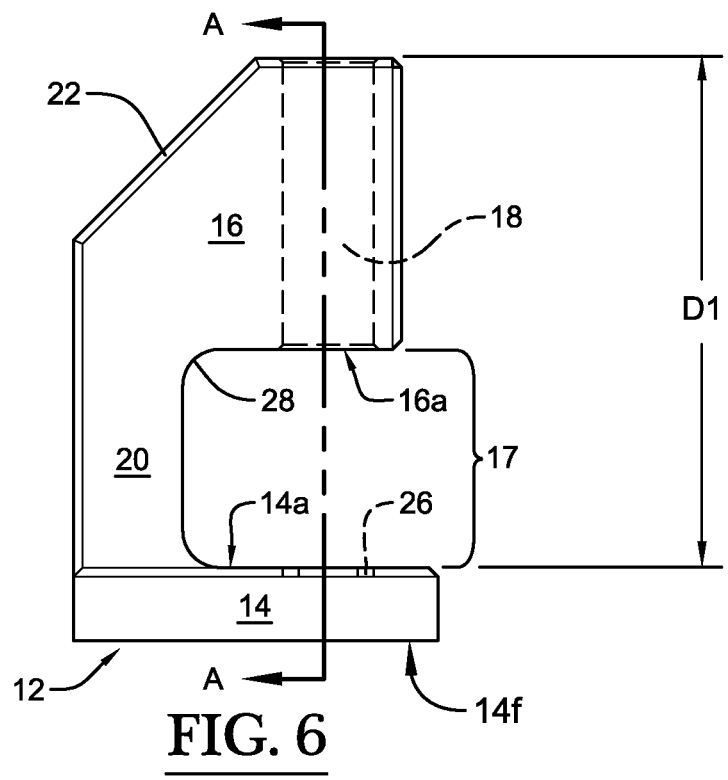
FIG. 6 is a side view of the guide stand of the orthopedic surgical instrument set according to an embodiment of the invention.
Figure 7:
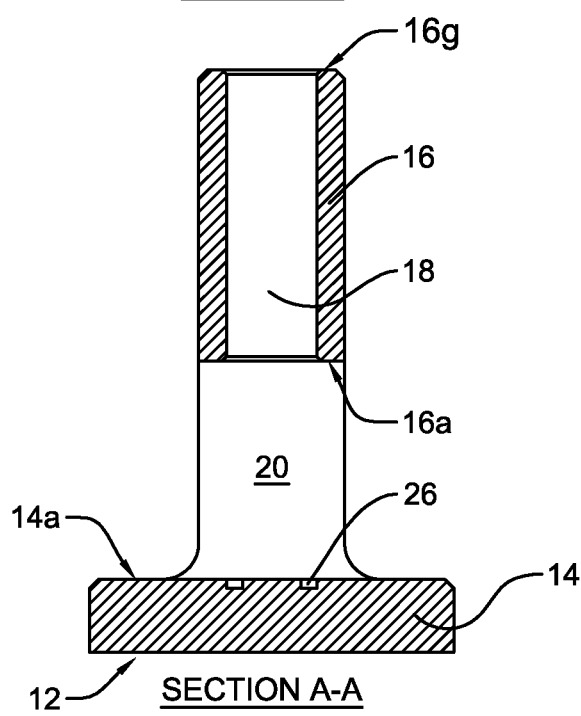
FIG. 7 is a sectional view of the guide stand of the orthopedic surgical instrument set according to an embodiment of the invention, which is cut along the cutting-plane line A-A in FIG. 6.

With reference to FIGS. 4-7, the guide stand 12 of the surgical instrument set 10 will be described in detail. In the illustrated embodiment, the guide stand 12 comprises a base portion 14 and an upper portion 16 disposed above the base portion 14. As best shown in FIGS. 4, 6, and 7, the upper portion 16 of the guide stand 12 is connected to the base portion 14 by means of a connecting portion 20. Also, it can be seen that a majority of the upper portion 16 of the guide stand 12 is disposed in a cantilevered manner above the base portion 14 thereof so as to form a gap 17 between the bottom surface 16a of the upper portion 16 and the top surface 14a of the base portion 14 (see FIG. 6). When the bone plug is being cut, a fragment of bone is placed in the gap 17 between the bottom surface 16a of the upper portion 16 and the top surface 14a of the base portion 14. Referring again to FIGS. 4-7, it can be seen that the upper portion 16 of the guide stand 12 is provided with a guide aperture 18 disposed therein for receiving one of the trephines 30, 40 in the surgical instrument set 10.

With reference to FIGS. 4-6, the geometry of the base portion 14 of the guide stand 12 will be described in detail. In the illustrated embodiment, the base portion 14 comprises a top surface 14a, a plurality of side surfaces 14b-14e, and a bottom surface 14f. As shown, each of the side surfaces 14b-14e is disposed at a substantially 90 degree angle with respect to the top and bottom surfaces 14a, 14f. The side surfaces 14b-14e of the base portion 14 of the guide stand 12 include a first side surface 14b, a second side surface 14c disposed opposite to the first side surface 14b, a third side surface 14d, and a fourth side surface 14e disposed opposite to the third side surface 14d. The first and second side surfaces 14b, 14c are disposed generally parallel to one another, and generally perpendicular to each of the third and fourth side surfaces 14d, 14e. Similarly, the third and fourth side surfaces 14d, 14e are disposed generally parallel to one another, and generally perpendicular to each of the first and second side surfaces 14b, 14c. As best shown in FIGS. 4 and 5, it can be seen that the base portion 14 of the guide stand 12 has a generally square footprint.

Next, with continued reference to FIGS. 4-6, the geometry of the upper portion 16 of the guide stand 12 will be described in detail. In the illustrated embodiment, the upper portion 16 comprises a bottom surface 16a, a plurality of side surfaces 16b-16e, an angled top surface 16f, and a generally flat top surface 16g. As shown, each of the side surfaces 16b-16e is disposed at a substantially 90 degree angle with respect to the bottom surface 16a and the flat top surface 16g. The side surfaces 16b-16e of the upper portion 16 of the guide stand 12 include a first side surface 16b, a second side surface 16c disposed opposite to the first side surface 16b, a third side surface 16d, and a fourth side surface 16e disposed opposite to the third side surface 16d. The first and second side surfaces 16b, 16c are disposed generally parallel to one another, and generally perpendicular to each of the third and fourth side surfaces 16d, 16e. Similarly, the third and fourth side surfaces 16d, 16e are disposed generally parallel to one another, and generally perpendicular to each of the first and second side surfaces 16b, 16c. As best shown in the perspective view of FIG. 4, the angled top surface 16f slopes downwardly from the edge of the flat top surface 16g to the top edge of the second side surface 16c.

In one or more embodiments, the base portion 14 and the upper portion 16 of the guide stand 12 are provided with chamfered edges 22 so as to eliminate sharp intersecting surfaces. Also, referring to FIGS. 4 and 6, it can be seen that a reinforcing filleted connection 24 is preferably provided between the base portion 14 and the connecting portion 20. Moreover, in order to reduce stress concentrations, a filleted corner 28 is provided at the location where the front side surface of the connecting portion 20 adjoins the bottom surface 16a of the upper portion 16.

Figure 12:
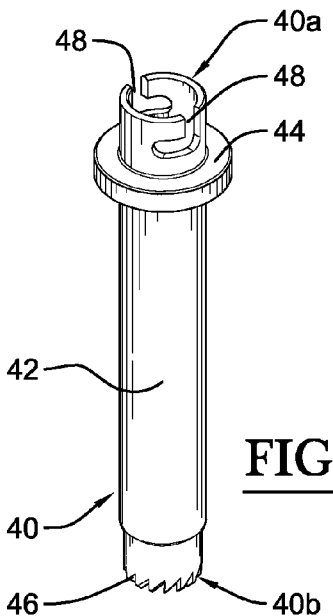
FIG. 12 is a perspective view of a second trephine of the orthopedic surgical instrument set according to an embodiment of the invention.
Figure 13:
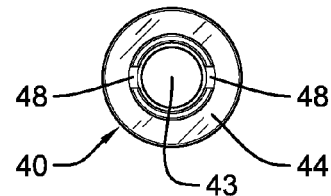
FIG. 13 is a top view of the second trephine of the orthopedic surgical instrument set according to an embodiment of the invention.
Figure 14:
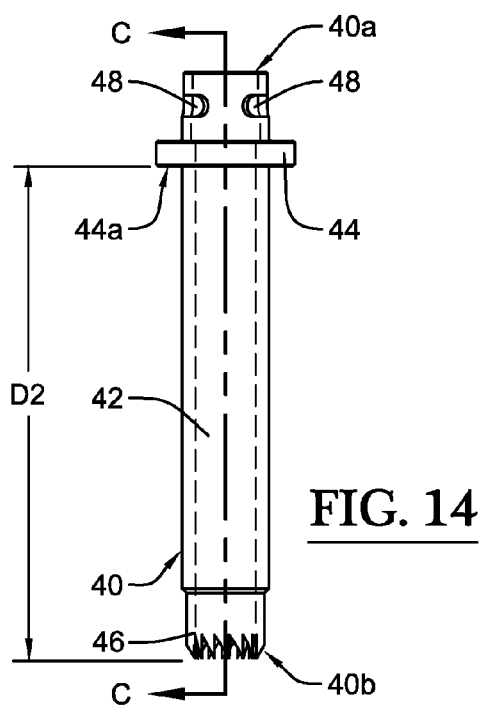
FIG. 14 is a side view of the second trephine of the orthopedic surgical instrument set according to an embodiment of the invention.
Figure 15:
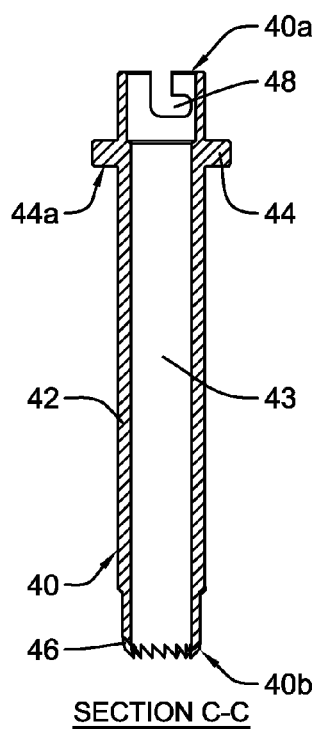
FIG. 15 is a sectional view of the second trephine of the orthopedic surgical instrument set according to an embodiment of the invention, which is cut along the cutting-plane line C-C in FIG. 14.

Advantageously, the guide stand 12 facilitates the cutting of the bone plug by preventing the trephine 30, 40 from veering off the bone target (i.e., the fragment of bone). In the illustrated embodiment, it can be seen that the base portion 14 of the guide stand 12 is provided with a kerf 26 disposed therein for receiving a second end 30b, 40b of the trephine 30, 40. In the depicted embodiment of the invention, the kerf 26 is in the form of an annular slot or groove. Although, in other embodiments of the invention, the kerf 26 is in the form of a cylindrical cavity. The kerf 26 in the base portion 14 of the guide stand 12 accepts the end 30b, 40b of each trephine 30, 40 so as to prevent the dulling of the cutting teeth 36, 46 disposed thereon (see e.g., FIGS. 8 and 12). More specifically, when the trephine 30, 40 is received within the guide aperture 18 of the guide stand 12 (e.g., as illustrated in FIG. 2), the pointed ends of the cutting teeth 36, 46 are received within the kerf 26, and thus, do not contact the top surface 14a of the base portion 14. A minimum suitable depth (e.g., 3 mm) is selected for the kerf 26 such that the pointed ends of the cutting teeth 36, 46 do not contact its bottom surface.

In a preferred embodiment, a vertical dimension D1 of the guide stand 12 measured between the top surface 14a of the base portion 14 and the generally flat top surface 16g of the upper portion 16 is slightly less than an axial length D2 of each trephine 30, 40 measured between a bottom surface 34a, 44a of the collar 34, 44 and the second end 30b, 40b of each trephine 30, 40. Maintaining the dimensional relationship between the guide stand 12 and each trephine 30, 40 allows the teeth 36, 46 of each trephine 30, 40 to be slightly recessed within the kerf 26. In one exemplary embodiment, the aforedescribed vertical dimension D1 of the guide stand 12 is approximately 1.0 millimeter (1 mm) less than the axial length D2 of each trephine 30, 40, as measured between a bottom surface 34a, 44a of the collar 34, 44 and the second end 30b, 40b of each trephine 30, 40. Although, those of ordinary skill in the art will readily appreciate that other suitable dimensional relationships between the guide stand 12 and the trephines 30, 40 can also be used.

In one exemplary embodiment, the base portion 14 of the guide stand 12 has an approximately two and one-half (2½) inch by two and one-half (2½) inch footprint and a height of approximately one-half (½) of an inch, while the guide stand 12 has an overall height of approximately four (4) inches. Although, it is to be understood that the invention is in no way limited to these particular dimensions. Rather, the invention may be practiced using any other suitable dimensions without departing from the spirit and scope of the appended claims.

Figure 8:
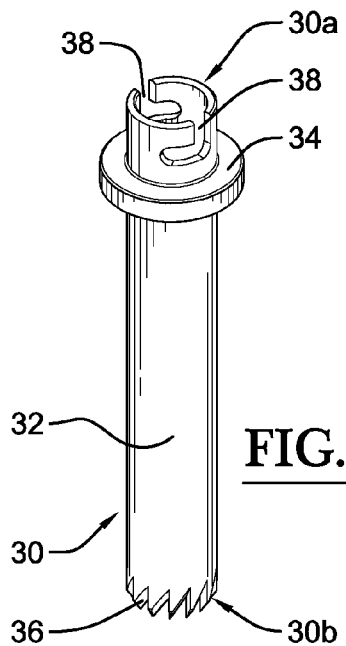
FIG. 8 is a perspective view of a first trephine of the orthopedic surgical instrument set according to an embodiment of the invention.
Figure 9:
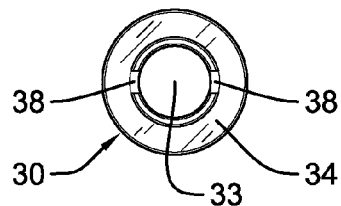
FIG. 9 is a top view of the first trephine of the orthopedic surgical instrument set according to an embodiment of the invention.
Figure 10:
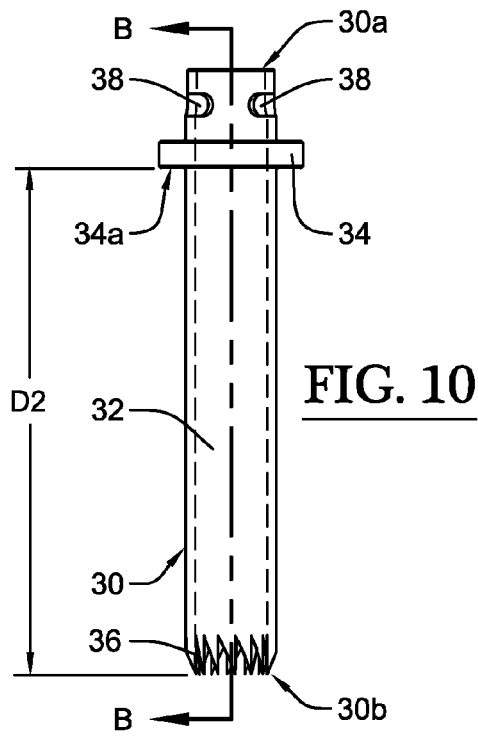
FIG. 10 is a side view of the first trephine of the orthopedic surgical instrument set according to an embodiment of the invention.
Figure 11:
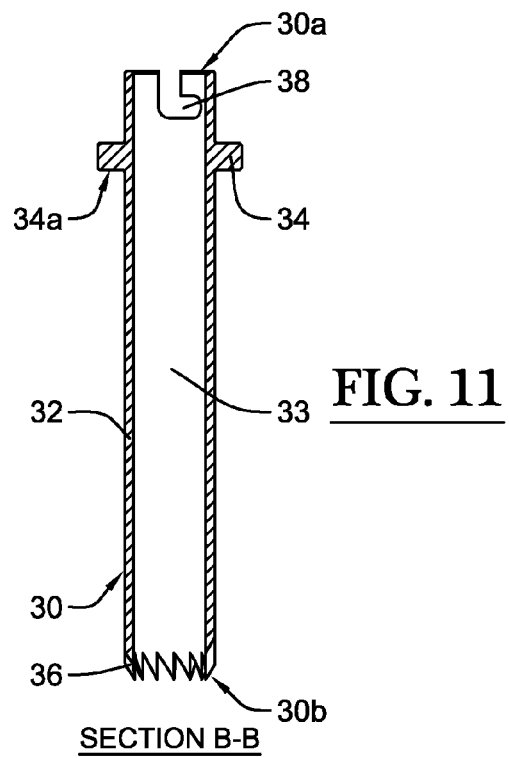
FIG. 11 is a sectional view of the first trephine of the orthopedic surgical instrument set according to an embodiment of the invention, which is cut along the cutting-plane line B-B in FIG. 10.

Now, turning to FIGS. 8-11, a first trephine 30 of the surgical instrument set 10 will be explained. As depicted in these figures, the first trephine 30 includes a substantially cylindrical body portion 32 with a cylindrical passageway 33 disposed therethrough. The diameter of the cylindrical passageway 33 of the first trephine 30 is sized to accommodate the substantially cylindrical body portion 52 of the first tamp 50 (i.e., the diameter of the cylindrical passageway 33 is slightly greater than the outer diameter of the cylindrical body portion 52 of the first tamp 50 so as to enable the sliding of the tamp 50 relative to the trephine 30). Referring to FIGS. 8, 10, and 11, it can be seen that the trephine 30 has opposed first and second ends 30a, 30b, with a plurality of cutting teeth 36 being disposed at the second end 30b thereof. In addition, it can be seen that the trephine 30 further includes a collar 34 disposed proximate to the first end 30a thereof. When the trephine 30 is inserted into the guide aperture 18 of the guide stand 12 (see FIG. 2), the bottom surface 34a of the collar 34 rests on the generally flat top surface 16g of the upper portion 16, thereby suspending the pointed ends of the cutting teeth 36 above the bottom surface of the kerf 26.

Moreover, as best shown in FIGS. 8 and 11, the first end 30a of the trephine 30 is provided with a plurality of elongated slots 38 cut therein. In the illustrated embodiment, it can be seen that each oppositely disposed elongated slot 38 is generally L-shaped with a rounded distal end. The elongated slots 38 of the trephine 30 are configured to matingly engage with the opposed protruding portions 60, 60' of the bit attachment members 56, 56', which are disposed proximate to the second ends of the bit attachment members 56, 56'. When the bit attachment member 56, 56' is being matingly engaged with the trephine 30, the opposed protruding portions 60, 60' of the bit attachment member 56, 56' are initially inserted into the axially extending portions of the elongated slots 38. After which, the bit attachment member 56, 56' is rotated clockwise relative to the trephine 30 to matingly engage the trephine 30 with the bit attachment member 56, 56' (i.e., the bit attachment member 56, 56' is rotated clockwise until its opposed protruding portions 60, 60' contact the respective rounded distal ends of the elongated slots 38). The bit attachment member 56, 56' remains connected with the trephine 30 during the clockwise rotation imparted on the members 30, 56 or 30, 56' by the drill operatively connected to the bit attachment member 56, 56'. In order to disengage the bit attachment member 56, 56' from the trephine 30, the bit attachment member 56, 56' can simply be rotated counter-clockwise by the drill.

Next, referring to FIGS. 12-15, a second trephine 40 of the surgical instrument set 10 will be described. Similar to the first trephine 30, the second trephine 40 includes a substantially cylindrical body portion 42 with a cylindrical passageway 43 disposed therethrough, a first end 40a with a collar 44 disposed proximate thereto, a second end 40b having a plurality of cutting teeth 46, and a plurality of elongated slots 48 cut in the first end 40a thereof for matingly engaging with the opposed protruding portions 60, 60' of the bit attachment members 56, 56'. However, the diameter of the cylindrical passageway 43 of the second trephine 40 is smaller than the diameter of the cylindrical passageway 33 of the first trephine 30. The diameter of the cylindrical passageway 43 of the second trephine 40 is sized to accommodate the smaller diameter substantially cylindrical body portion of the second tamp 50' (i.e., the diameter of the cylindrical passageway 43 is slightly greater than the outer diameter of the cylindrical body portion of the second tamp 50' so as to enable the sliding of the tamp 50' relative to the trephine 40). Like the first trephine 30, when the second trephine 40 is inserted into the guide aperture 18 of the guide stand 12 (see FIG. 2), the bottom surface 44a of the collar 44 rests on the generally flat top surface 16g of the upper portion 16, thereby suspending the pointed ends of the cutting teeth 46 above the bottom surface of the kerf 26.

In one exemplary embodiment, the cylindrical passageways 33, 43 of the first and second trephines 30, 40 have inside diameters of approximately 11 mm and 9 mm, respectively, in order to accommodate the standard holes created by 10 mm and 8 mm intramedullary rods that are used in knee arthroplasty systems (i.e., the fabricated bone plug is approximately 1 mm greater than the hole size to provide a friction fit therein). Also, in one exemplary embodiment, the first and second trephines 30, 40 have an overall length of approximately four and one-quarter (4¼) inches, and the upper surfaces of the collars 34, 44 of the trephines 30, 40 are spaced apart from the first ends 30a, 40a of the trephines 30, 40 by a distance of approximately one-half (½) inch in the axial direction. Although, it is to be understood that the invention is in no way limited to these particular dimensions. Rather, the invention may be practiced using any other suitable dimensions without departing from the spirit and scope of the appended claims.

Figure 16:
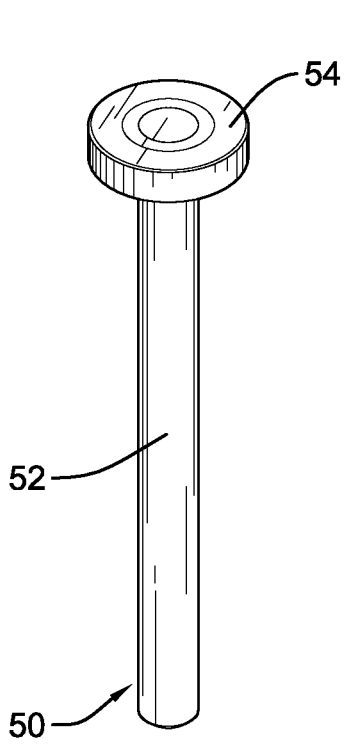
FIG. 16 is a perspective view of a tamp of the orthopedic surgical instrument set according to an embodiment of the invention.
Figure 17:
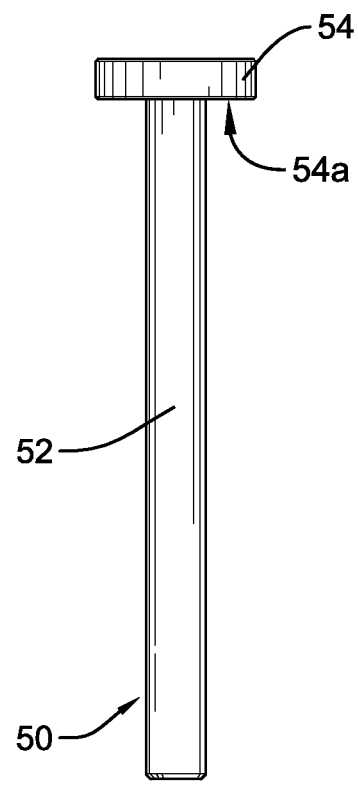
FIG. 17 is a side view of the tamp of the orthopedic surgical instrument set according to an embodiment of the invention.
Figure 18:
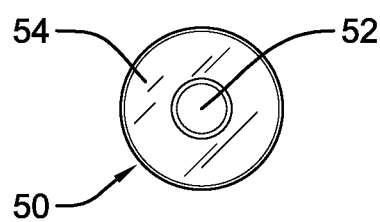
FIG. 18 is a bottom view of the tamp of the orthopedic surgical instrument set according to an embodiment of the invention.
Figure 22:
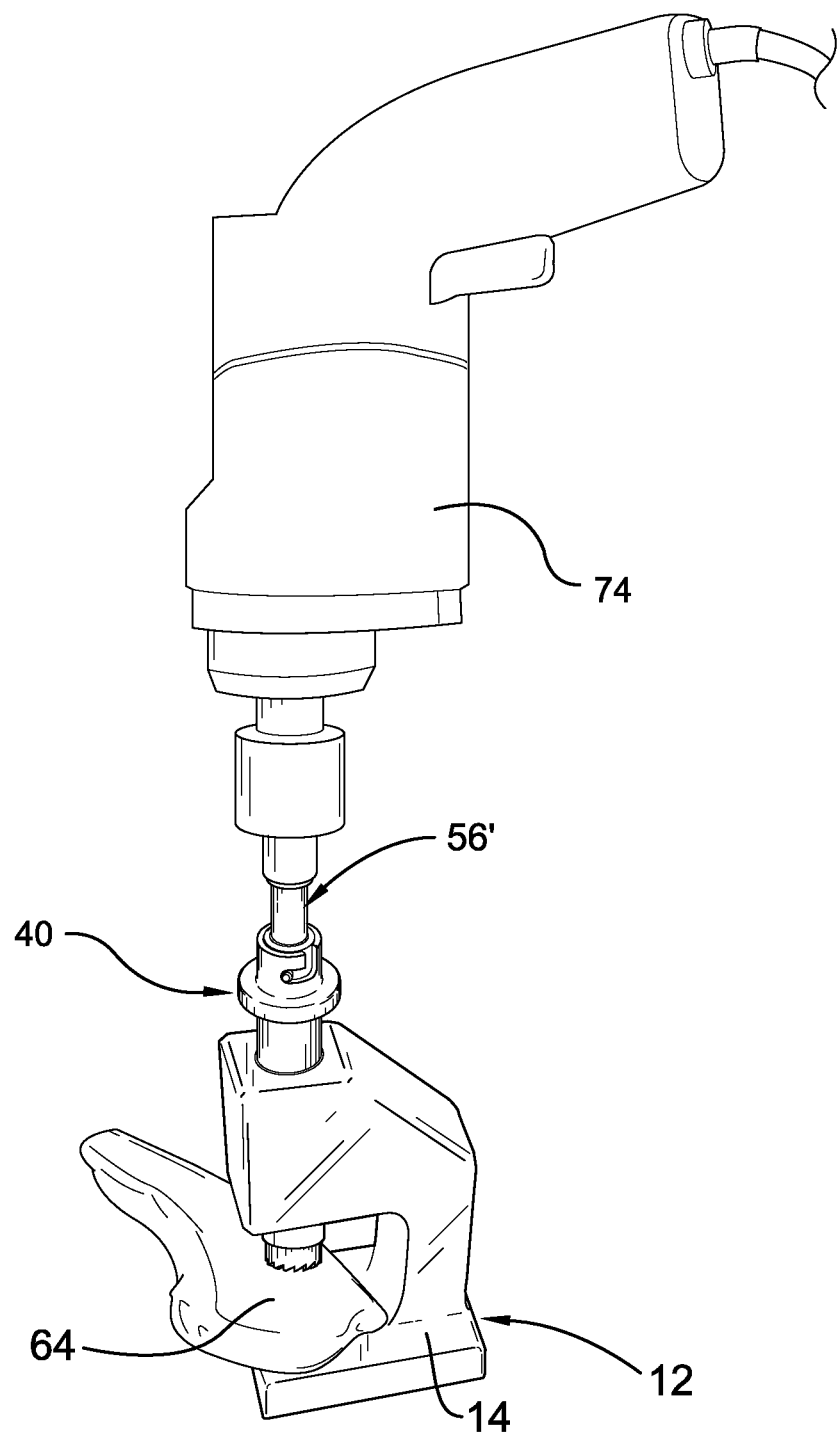
FIG. 22 is a perspective view illustrating the manner in which components of the orthopedic surgical instrument set can be used to cut a plug from a piece of bone, according to an embodiment of the invention.
Figure 23:
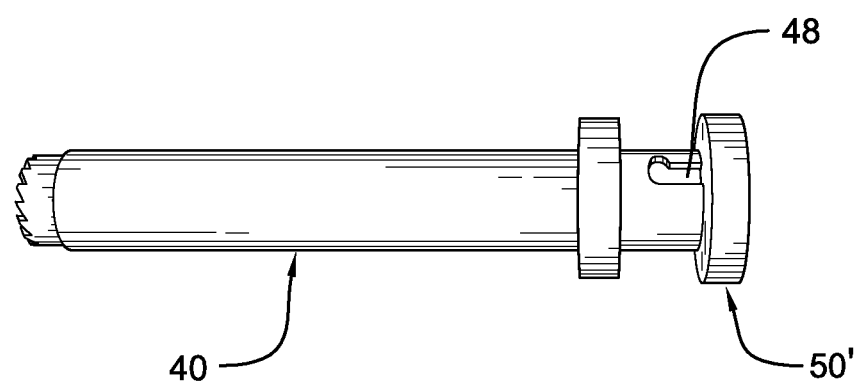
FIG. 23 is a perspective view illustrating the manner in which the tamp of the orthopedic surgical instrument set can be inserted into the trephine, according to an embodiment of the invention.

Referring to FIGS. 16-18, the tamp 50 of the surgical instrument set 10 will now be explained. As depicted in these figures, the tamp 50 includes a substantially cylindrical body portion 52 with a substantially cylindrical head 54 disposed at the upper end thereof. It can be seen that the substantially cylindrical head 54 of the tamp 50 has an outer diameter than is substantially greater than the outer diameter of the substantially cylindrical body portion 52. Preferably, the axial length of the substantially cylindrical body portion 52 of the tamp 50 is substantially equal to the axial length of the cylindrical passageway 33 of the trephine 30. As such, when the tamp 50 is inserted into the trephine 30, the cylindrical body portion 52 of the tamp 50 will substantially fill the cylindrical passageway 33 of the trephine 30. Also, when the tamp 50 is fully inserted into the trephine 30, the bottom surface 54a of its cylindrical head 54 abuts the top annular surface of the trephine 30 (see e.g., FIG. 23 for fully inserted position) and its distal end lies substantially flush with the distal, second end 30b of the trephine 30.

After the bone plug has been cut from the fragment of bone using the trephine 30, the tamp 50 is used to eject the bone plug from the cylindrical passageway 33 of the trephine 30, and to insert the bone plug in the aperture of the femur that is being filled thereby.

In one exemplary embodiment, the cylindrical body portions of the first and second tamps 50, 50' have inside diameters of approximately 10 mm and 8 mm, respectively, in order to fit within respective 11 mm and 9 mm diameter cylindrical passageways 33, 43 of the first and second trephines 30, 40 (i.e., 1 mm is allowed for clearance). Also, in one exemplary embodiment, the tamps 50, 50' have an overall length of approximately four and one-half (4½) inches, while the cylindrical body portions of the tamps 50, 50' have a length of approximately four and one-quarter (4¼) inches. Although, it is to be understood that the invention is in no way limited to these particular dimensions. Rather, the invention may be practiced using any other suitable dimensions without departing from the spirit and scope of the appended claims.

Next, with reference to FIGS. 19-21, one embodiment of the bit attachment member or driver 56 of the surgical instrument set 10 will be explained. As illustrated in these figures, the bit attachment member 56 generally comprises a substantially cylindrical base portion 58 that is connected to a bit portion 62 having a substantially hexagonal shape. As best shown in FIGS. 19 and 20, the substantially cylindrical base portion 58 of the bit attachment member 56 is provided with opposed protruding portions 60 for respectively engaging the elongated slots 38, 48 in the first and second trephines 30, 40. In the illustrated embodiment, the opposed protruding portions 60 are generally centrally disposed along the length of the cylindrical base portion 58 in an axial direction.

Referring to FIGS. 19 and 21, it can be seen that the bit attachment member 56 has opposed first and second ends 56a, 56b. The first end 56a of the bit attachment member 56 is configured to engage with a chuck of a surgical drill, while the second end 56b of the bit attachment member 56 is configured to engage with the first ends 30a, 40a of the trephines 30, 40 (i.e., when the opposed protruding portions 60 engage with the elongated slots 38, 48).

In one embodiment of the invention, the opposed protruding portions 60 can be integrally formed with the cylindrical base portion 58 of the bit attachment member 56. In another embodiment, the opposed protruding portions 60 can be formed by a separate rod that is disposed through a diametrically extending aperture in the cylindrical base portion 58 of the bit attachment member 56.

In one exemplary embodiment, the bit attachment member 56 has an overall length of approximately one and one-half (1½) inches, the bit portion 62 of the bit attachment member 56 has a length of approximately one (1) inch, and the centers of the opposed protruding portions 60 are spaced approximately one-quarter (¼) of an inch from the second end 56b of the bit attachment member 56 in the axial direction. Although, it is to be understood that the invention is in no way limited to these particular dimensions. Rather, the invention may be practiced using any other suitable dimensions without departing from the spirit and scope of the appended claims.

Figure 26:
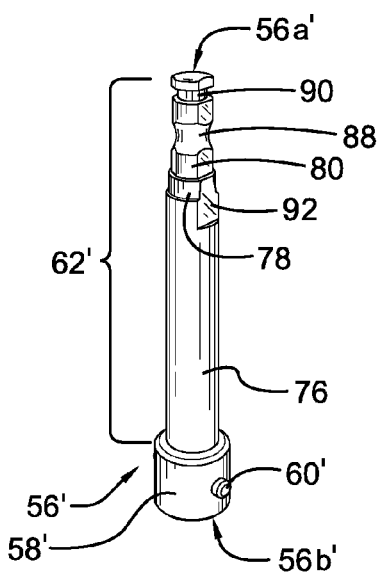
FIG. 26 is a perspective view of an alternative bit attachment member of the orthopedic surgical instrument set according to an embodiment of the invention.
Figure 27:
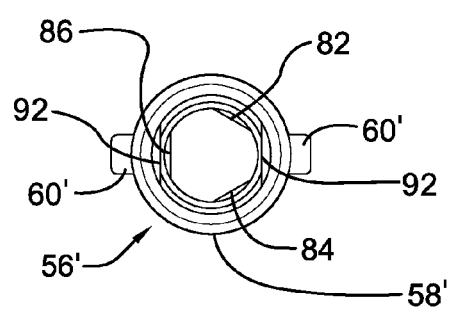
FIG. 27 is a top view of the alternative bit attachment member of the orthopedic surgical instrument set according to an embodiment of the invention.

Referring to FIGS. 26 and 27, another embodiment of the bit attachment member or driver 56' of the surgical instrument set 10 will be described. As illustrated in these figures, the bit attachment member 56' generally comprises a substantially cylindrical base portion 58' that is connected to a bit portion 62'. As shown in FIGS. 26 and 27, like the substantially cylindrical base portion 58 of the bit attachment member 56, the substantially cylindrical base portion 58' of the bit attachment member 56' is provided with opposed protruding portions 60' for respectively engaging the elongated slots 38, 48 in the first and second trephines 30, 40. In the illustrated embodiment, the opposed protruding portions 60' are generally centrally disposed along the length of the cylindrical base portion 58' in an axial direction. Based upon the particular surgical drill that is being utilized, the surgeon would select one of the bit attachment members 56, 56' to connect the drill chuck to each of the trephines 30, 40.

Like the bit attachment member 56 described above, it can be seen that the bit attachment member 56' also has opposed first and second ends 56a', 56b'. The first end 56a' of the bit attachment member 56' is configured to engage with a chuck of a surgical drill, while the second end 56b' of the bit attachment member 56' is configured to engage with the first ends 30a, 40a of the trephines 30, 40 (i.e., when the opposed protruding portions 60' engage with the elongated slots 38, 48). However, the configuration of the bit portion 62' of the bit attachment member 56' is quite different from that of the bit attachment member 56. As best shown in FIG. 26, the bit portion 62' comprises three (3) generally cylindrical bit sections 76, 78, 80. The first bit section 76 has the largest diameter, the third bit section 80 has the smallest diameter, and the second bit section 78 has a diametric size in between the first bit section 76 and third bit section 80. With continued reference to FIG. 26, it can be seen that the upper end portion of the bit portion 62' is provided with first and second annular grooves 88, 90, which are axially spaced apart from one another. Each of the grooves 88, 90 is disposed in the third bit section 80, but the second annular groove 90 is disposed closest to the first end 56a' of the bit attachment member 56', while the first annular groove 88 is disposed closer to the second bit section 78.

In addition, the upper end portion of the bit portion 62' of the bit attachment member 56' is provided with multiple pluralities of faceted faces 82, 84, 86, 92. Referring to FIGS. 26 and 27, it can be seen that the third bit section 80 is provided with a first plurality of faceted faces 82 (separated by grooves 88 and 90), a second plurality of faceted faces 84 (separated by grooves 88 and 90), and a third plurality of faceted faces 86 (separated by grooves 88 and 90). In the top view of FIG. 27, it can be seen that the pluralities of faceted faces 82, 84, 86 are generally equally spaced apart from another by approximately 120 degrees about the circumference of the third bit section 80. In addition, the bit portion 62' is provided with opposed faceted faces 92, which overlap its first and second bit sections 76, 78. As shown in FIG. 27, the opposed faceted faces 92 are generally spaced apart from another by approximately 180 degrees about the circumference of the first and second bit sections 76, 78.

In one embodiment of the invention, the components of the orthopedic surgical instrument set 10 are formed from one or more suitable metals. For example, in one exemplary embodiment, the guide stand 12 is formed from 6061 aluminum alloy. As another example, in one exemplary embodiment, the trephines 30, 40 are formed from 440C stainless steel. Although, those of ordinary skill in the art will appreciate that the components of the orthopedic surgical instrument set 10 can be formed from various other suitable materials, provided that the selected materials are suitably durable and appropriate for use in surgical procedures.

Now, referring to FIGS. 22-25, the manner in which components of the orthopedic surgical instrument set 10 are used to fabricate a bone plug will be described in detail. Initially, a user places a removed fragment of bone (e.g., femoral condyle, tibial plateau, or patellar fragment) on the base portion 14 of the guide stand 12, overlying the receiving kerf 26 (see FIG. 22, the piece of bone 64 in this figure is generally in the form of a bone fragment). The base portion 14 of the guide stand 12 operates as a cutting block. Next, after the trephine 40 is positioned in the guide aperture 18 of the upper portion 16 of the guide stand 12 by the user, the cutting teeth 46 of the trephine 40 are driven through the bone fragment 64 using a convention surgical drill 74, which is operatively coupled to the trephine by means of the bit attachment member 56, 56'. After the user cuts through the bone fragment 64 using the surgical drill 74, a core of bone 70 then remains inside the trephine 40 (see e.g., FIG. 24). Preferably, as discussed above, the depth from the generally flat top surface 16g of the upper portion of the guide stand 12 to the bottom of the receiving kerf 26 is slightly longer than the length of the body portion 42 of the trephine 40 extending from the bottom surface 44a of the collar 44 to the second end 40b of the trephine 40. This prevents the trephine 40 from ever making contact with another surface, thereby preserving the sharpness of the instrument.

Figure 24:
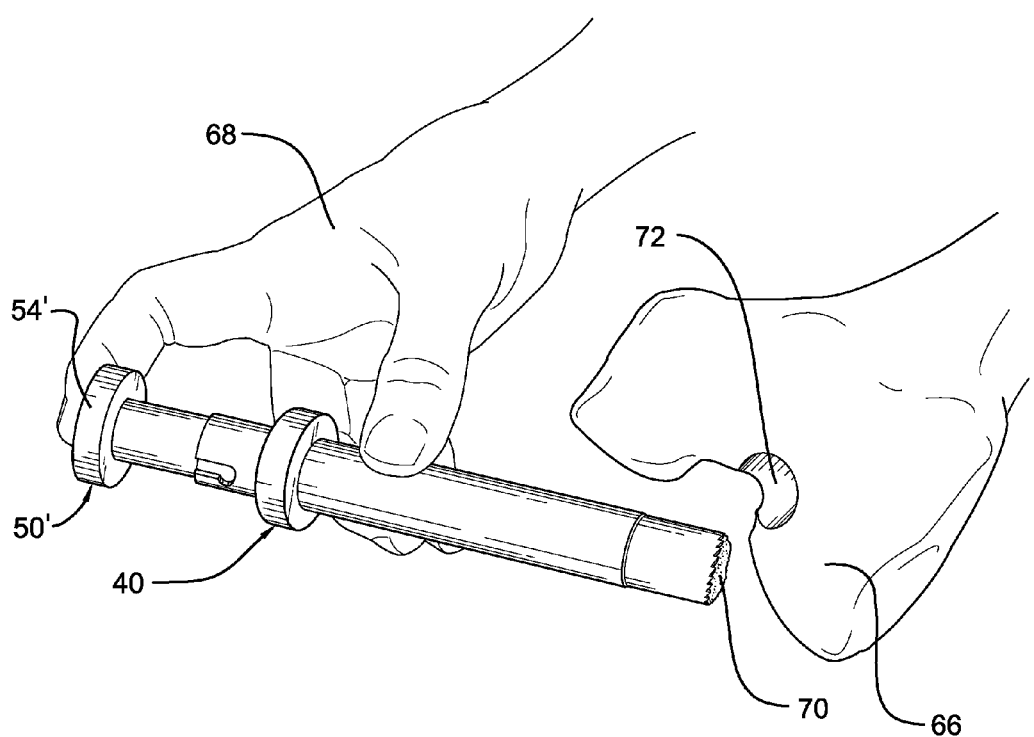
FIG. 24 is a perspective view illustrating the manner in which the trephine and tamp of the orthopedic surgical instrument set can be used to introduce a bone plug for insertion into a bone aperture, according to an embodiment of the invention.
Figure 25:
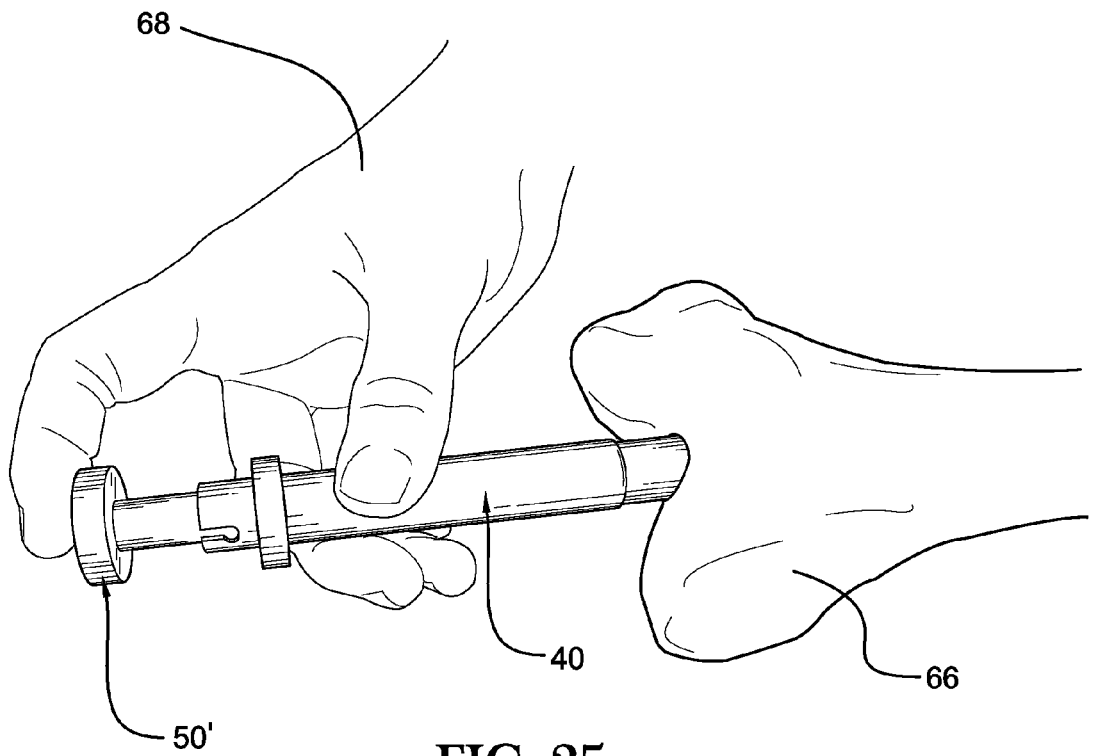
FIG. 25 is a perspective view illustrating the manner in which the trephine and tamp of the orthopedic surgical instrument set can be used to insert a bone plug into a bone aperture, according to an embodiment of the invention.

Next, referring to FIGS. 24 and 25, the user disconnects the trephine 40, which contains the bone plug 70, from the bit attachment member 56' and inserts the tamp 50' therein. Then, the user 68 positions the trephine 40 over the femoral hole 72 in the femur 66, and he or she uses finger pressure or a mallet to apply a force to the tamp 50' so as to drive the bone plug 70 tightly into the hole 72. Once the tamp head or cap 54' reaches the annular top surface of the trephine 40, the bone plug 70 is generally fully inserted into the femoral hole 72. The head 54' of the tamp 50' prevents the over-insertion of the bone plug 70. In a preferred embodiment, the entire process of fabricating and inserting the bone plug 70 takes approximately 10-15 seconds. While the bone plug fabrication method has been described in conjunction with the trephine 40, it is to be understood that all of the steps described above can be performed in the same manner using the trephine 30, which produces a large diameter bone plug (i.e., an approximately 11 mm diameter bone plug, as compared to the approximately 9 mm diameter bone plug produced by the trephine 40).

It is readily apparent that the aforedescribed orthopedic surgical instrument set 10 offers numerous advantages. First, the orthopedic surgical instrument set 10 can be used to quickly harvest and introduce a bone plug 70 for substantially filling and sealing the distal femoral intramedullary hole in total knee replacement arthroplasty. The instrument set 10 is capable of using a piece of bone that is normally discarded. Secondly, the orthopedic surgical instrument set 10 described herein enables a slightly oversized bone plug to be quickly produced on the back table in an operating room, and easily inserted into the distal femoral hole by a surgeon. Finally, the surgical instrument set 10 heretofore described can be used with a conventional orthopedic drill, thereby obviating the need to purchase a special surgical drill.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An orthopedic surgical instrument set comprising, in combination:

at least one tamp, said tamp including a substantially cylindrical body portion;

at least one trephine, said trephine having a first end and a second end, said second end of said trephine having a plurality of teeth disposed thereon, said trephine being provided with a cylindrical passageway disposed therethrough for receiving said substantially cylindrical body portion of said tamp; and a guide stand having a base portion with a top surface and an upper portion disposed above said base portion, said upper portion including a first lateral side and a second lateral side, said top surface of said base portion of said guide stand being provided with a kerf disposed therein for receiving said second end of said at least one trephine, said kerf in said top surface of said base portion being in the form of a circular bore with a circular sidewall disposed about a central axis and a bottom surface recessed below said top surface of said base portion, said upper portion of said guide stand including a cantilevered portion with a bottom surface that extends above, and faces said top surface of said base portion, said cantilevered portion of said upper portion of said guide stand being provided with a guide aperture disposed therein for receiving said at least one trephine, said guide aperture disposed about said central axis of said kerf.

2. The orthopedic surgical instrument set according to claim 1, wherein said at least one tamp further includes a cylindrical head located at one end of said substantially cylindrical body portion, said cylindrical head having an outer diameter that is greater than that of said substantially cylindrical body portion.

3. The orthopedic surgical instrument set according to claim 2, wherein an axial length of said cylindrical passageway of said at least one trephine is substantially equal to an axial length of said substantially cylindrical body portion of said at least one tamp.

4. The orthopedic surgical instrument set according to claim 2, wherein said at least one trephine further includes at least one slot cut into said first end thereof and a protruding collar disposed proximate to said first end, said protruding collar comprising an annular projection extending outwardly from an outer circular sidewall of said at least one trephine, said protruding collar being spaced apart from said first end of said at least one trephine by a distance, and said protruding collar being disposed beneath said at least one slot.

5. The orthopedic surgical instrument set according to claim 4 wherein, when said at least one tamp is fully inserted into said at least one trephine, a bottom surface of said cylindrical head of said at least one tamp abuts a top annular surface of said at least one trephine and is spaced apart from said protruding collar of said at least one trephine by said distance.

6. The orthopedic surgical instrument set according to claim 1, wherein said at least one trephine further includes a plurality of L-shaped slots cut in said first end thereof.

7. The orthopedic surgical instrument set according to claim 6 further comprising a bit attachment member, said bit attachment member having a first end and a second end, said first end of said bit attachment member being configured to engage with a chuck of a surgical drill, said second end of said bit attachment member having opposed protruding portions disposed proximate thereto.

8. The orthopedic surgical instrument set according to claim 7, wherein each of said opposed protruding portions of said bit attachment member are configured to matingly engage with a respective one of said plurality of L-shaped slots in said at least one trephine.

9. The orthopedic surgical instrument set according to claim 1, wherein said at least one tamp comprises two tamps and said at least one trephine comprises two trephines, and wherein:
   said substantially cylindrical body portion of a first of said two tamps has a first outside diameter;
   said substantially cylindrical body portion of a second of said two tamps has a second outside diameter that is larger than said first outside diameter of said first tamp;
   said cylindrical passageway of a first of said two trephines has a first inner diameter that is slightly larger than said first outside diameter of said first tamp; and
   said cylindrical passageway of a second of said two trephines has a second inner diameter that is slightly larger than said second outside diameter of said second tamp.

10. The orthopedic surgical instrument set according to claim 1, wherein said guide stand further includes a connecting portion disposed between said base portion and said upper portion, said connecting portion including a first lateral side and a second lateral side.

11. The orthopedic surgical instrument set according to claim 10, wherein said upper portion of said guide stand is spaced apart from said base portion of said guide stand by said connecting portion such that a gap is defined between said bottom surface of said cantilevered portion of said upper portion and said top surface of said base portion, and wherein said first and second lateral sides of said upper portion are co-planar with said first and second lateral sides of said connecting portion.

12. The orthopedic surgical instrument set according to claim 11, wherein said at least one trephine further includes at least one slot cut into said first end thereof and a protruding collar disposed proximate to said first end, said protruding collar comprising an annular projection extending outwardly from an outer circular sidewall of said at least one trephine, said protruding collar being spaced apart from said first end of said at least one trephine by a distance, and said protruding collar being disposed beneath said at least one slot.

13. The orthopedic surgical instrument set according to claim 12, wherein a vertical dimension of said guide stand measured between said top surface of said base portion and a top surface of said upper portion is slightly less than an axial length of said at least one trephine measured between a bottom surface of said collar and said second end of said at least one trephine.

14. The orthopedic surgical instrument set according to claim 1, wherein said kerf in said top surface of said base portion is disposed beneath said guide aperture in said cantilevered portion of said upper portion of said guide stand.

15. The orthopedic surgical instrument set according to claim 14, wherein said kerf is in the form of one of: (i) an annular slot and (ii) a cylindrical cavity.

16. An orthopedic surgical instrument set comprising, in combination:
   at least one tamp, said tamp including a substantially cylindrical body portion;
   at least one trephine, said trephine having a first end and a second end, said second end of said trephine having a plurality of teeth disposed thereon, said trephine being provided with a cylindrical passageway disposed therethrough for receiving said substantially cylindrical body portion of said tamp, said at least one trephine further including at least one slot cut into said first end thereof and a protruding collar disposed proximate to said first end, said protruding collar comprising an annular projection extending outwardly from an outer circular sidewall of said at least one trephine, said protruding collar being spaced apart from said first end of said at least one trephine by a distance, and said protruding collar being disposed beneath said at least one slot; and
   a guide stand having a base portion with a top surface, an upper portion disposed above said base portion, and a connecting portion disposed between said base portion and said upper portion, said top surface of said base portion of said guide stand being provided with a kerf disposed therein for receiving said second end of said at least one trephine, said kerf in said top surface of said base portion being in the form of a circular bore with a circular sidewall and a bottom surface recessed below said top surface of said base portion, said upper portion of said guide stand including a cantilevered portion with a bottom surface that extends above, and faces said top surface of said base portion, said cantilevered portion of said upper portion of said guide stand being provided with a guide aperture disposed therein for receiving said at least one trephine, and said upper portion of said guide stand being spaced apart from said base portion of said guide stand by said connecting portion such that a gap is defined between said bottom surface of said cantilevered portion of said upper portion and said top surface of said base portion.

17. A method of fabricating a bone plug for use during an orthopedic surgical procedure, said method comprising the steps of:

providing an orthopedic surgical instrument set that includes:

at least one tamp, said tamp including a substantially cylindrical body portion;

at least one trephine, said trephine having a first end and a second end, said second end of said trephine having a plurality of teeth disposed thereon, said trephine being provided with a cylindrical passageway disposed therethrough for receiving said substantially cylindrical body portion of said tamp; and a guide stand having a base portion with a top surface and an upper portion disposed above said base portion, said upper portion including a first lateral side and a second lateral side, said top surface of said base portion of said guide stand being provided with a kerf disposed therein for receiving said second end of said at least one trephine, said kerf in said top surface of said base portion being in the form of a circular bore with a circular sidewall disposed about a central axis and a bottom surface recessed below said top surface of said base portion, said upper portion of said guide stand including a cantilevered portion with a bottom surface that extends above, and faces said top surface of said base portion, said cantilevered portion of said upper portion of said guide stand being provided with a guide aperture disposed therein for receiving said at least one trephine, said guide aperture disposed about said central axis of said kerf;

positioning a fragment of bone on said top surface of said base portion of said guide stand;

positioning said at least one trephine in said guide aperture of said cantilevered portion of said upper portion of said guide stand;

cutting a bone plug from said fragment of bone by driving said plurality of teeth on said second end of said at least one trephine into said fragment of bone;

removing said at least one trephine containing said bone plug from said guide stand;

inserting said at least one tamp into said at least one trephine;

positioning said at least one trephine containing said bone plug over an aperture in a bone of patient; and driving said bone plug into said aperture of said bone of said patent by applying a force to an end of said at least one tamp.

18. The method according to claim 17, wherein the step of positioning said fragment of bone further comprises positioning said fragment of bone on said base portion of said guide stand overlying said kerf.

19. The method according to claim 17, further comprising the steps of:

providing a bit attachment member, said bit attachment member having a first end and a second end, said first end of said bit attachment member being configured to engage with a chuck of a surgical drill, said second end of said bit attachment member being configured to engage with said first end of said at least one trephine;

providing a surgical drill having a chuck that is rotatably driven by a motor;

engaging said first end of said bit attachment member with said chuck of said surgical drill;

engaging said second end of said bit attachment member with said first end of said at least one trephine; and driving said plurality of teeth on said second end of said at least one trephine into said fragment of bone by rotating said at least one trephine using said surgical drill.

20. The method according to claim 17, wherein a mallet is provided for applying said force to said at least one tamp; and wherein the step of driving said bone plug into said aperture further comprises driving said bone plug into said aperture of said bone of said patent by applying said force to said end of said at least one tamp by using said mallet.

* * * * *